US009212114B2

(12) United States Patent
Cassidy et al.

(10) Patent No.: US 9,212,114 B2
(45) Date of Patent: Dec. 15, 2015

(54) PROCESS FOR THE PRODUCTION OF A FATTY ALCOHOL FROM A FATTY ACID

(71) Applicant: Johnson Matthey Davy Technologies Limited, London (GB)

(72) Inventors: Paul John Cassidy, London (GB); Robert Wild, Thornaby (GB); Rikard Umberto Andersson, London (GB); Simon Nicholas Tilley, Thornaby (GB); Adrian Backes, London (GB)

(73) Assignee: JOHNSON MATTHEY DAVY TECHNOLOGIES LIMITED, London (GB)

( * ) Notice: Subject to any disclaimer, the term of this patent is extended or adjusted under 35 U.S.C. 154(b) by 0 days.

(21) Appl. No.: 14/432,258

(22) PCT Filed: Oct. 3, 2013

(86) PCT No.: PCT/GB2013/052584
§ 371 (c)(1),
(2) Date: Mar. 30, 2015

(87) PCT Pub. No.: WO2014/057248
PCT Pub. Date: Apr. 17, 2014

(65) Prior Publication Data
US 2015/0291491 A1     Oct. 15, 2015

(30) Foreign Application Priority Data
Oct. 9, 2012   (GB) .................................. 1218078.2

(51) Int. Cl.
*C07C 29/17*       (2006.01)
*C07C 29/128*      (2006.01)
C07C 31/125        (2006.01)
C07C 29/80         (2006.01)
C07C 29/149        (2006.01)

(52) U.S. Cl.
CPC .............. *C07C 29/17* (2013.01); *C07C 29/128* (2013.01); *C07C 29/149* (2013.01); *C07C 29/80* (2013.01); *C07C 31/125* (2013.01)

(58) Field of Classification Search
CPC .... C07C 29/128; C07C 29/149; C07C 29/80; C07C 31/125
USPC ................................................. 568/877, 885
See application file for complete search history.

(56) References Cited

U.S. PATENT DOCUMENTS

| 4,681,967 | A | 7/1987 | Green |
| 5,138,106 | A | 8/1992 | Wilmott et al. |
| 5,157,168 | A | 10/1992 | Wilmott et al. |
| 5,436,357 | A | 7/1995 | Jiang et al. |
| 5,536,856 | A | 7/1996 | Harrison et al. |
| 5,561,205 | A | 10/1996 | Jiang et al. |
| 5,672,781 | A | 9/1997 | Koehler et al. |
| 6,147,196 | A | 11/2000 | Stern et al. |
| 6,187,974 | B1 | 2/2001 | Wieczorek et al. |
| 6,204,424 | B1 | 3/2001 | Yadav et al. |
| 6,316,654 | B1 | 11/2001 | Honnick et al. |
| 6,359,157 | B2 | 3/2002 | Peter et al. |
| 6,376,701 | B1 | 4/2002 | Chavan et al. |
| 6,743,942 | B1 | 6/2004 | Palaniappan et al. |
| 6,933,398 | B2 | 8/2005 | Peter et al. |
| 6,979,748 | B2 | 12/2005 | Houben et al. |
| 7,030,057 | B2 | 4/2006 | Matsumoto |
| 7,078,560 | B2 | 7/2006 | Houben et al. |
| 7,122,688 | B2 | 10/2006 | Lin et al. |
| 7,211,681 | B2 | 5/2007 | Furuta |
| 2008/0021232 | A1 | 1/2008 | Lin et al. |
| 2011/0054225 | A1 | 3/2011 | Boensch et al. |

FOREIGN PATENT DOCUMENTS

| EP | 0523461 A2 | 1/1993 |
| EP | 0646567 A2 | 5/1995 |
| EP | 0781758 A1 | 2/1997 |
| EP | 1640356 A1 | 3/2006 |
| EP | 1785478 A1 | 5/2007 |
| GB | 2116552 B | 9/1985 |
| WO | 8203854 | 11/1982 |
| WO | 9410112 | 5/1994 |
| WO | 9828256 | 7/1998 |
| WO | 9947483 | 9/1999 |
| WO | 03020782 A2 | 3/2003 |
| WO | 2004085583 A1 | 10/2004 |
| WO | 2005100306 A1 | 10/2005 |
| WO | 2006013080 A1 | 2/2006 |
| WO | 2006029655 A1 | 3/2006 |
| WO | 2006050925 A1 | 5/2006 |
| WO | 2006070661 A1 | 7/2006 |
| WO | 2006129435 A1 | 12/2006 |
| WO | 2006133437 A1 | 12/2006 |
| WO | 2007006569 A1 | 1/2007 |
| WO | 2007025360 A2 | 3/2007 |
| WO | 2007043062 A1 | 4/2007 |
| WO | 2007074592 A1 | 7/2007 |
| WO | 2007111604 A1 | 10/2007 |
| WO | 2010096626 A1 | 8/2010 |
| WO | 2013072664 A1 | 5/2013 |

OTHER PUBLICATIONS

International Search Report and Written Opinion of PCT/GB2013/052584, dated Dec. 10, 2013, 12 pages.

*Primary Examiner* — Elvis O Price
(74) *Attorney, Agent, or Firm* — Armstrong Teasdale LLP

(57) ABSTRACT

In a process for producing fatty alcohol, fatty acid is subjected to esterification with a lower alkanol to form a stream of lower alkyl fatty acid ester(s). The stream is vaporized and then subjected to hydrogenation. The stream is then subjected to transesterification in a wax ester reactor to convert at least a portion of the lower alkyl fatty acid ester(s) to lower alkanol and wax ester(s). The resulting stream is then separated to yield a fatty alcohol(s) steam, a wax ester(s) stream, and an overhead stream comprising fatty alkanol(s) and alkane. The overhead stream is reacted in a wax ester reactor to convert at least a portion of the lower alkyl fatty acid ester to lower alkanol and wax ester(s). The wax ester(s) formed from the alkane is separated, along with any water and/or lower alkanol present.

13 Claims, 3 Drawing Sheets

PROCESS FOR THE PRODUCTION OF A FATTY ALCOHOL FROM A FATTY ACID

The present invention relates to a process for the production of fatty alcohols. More particularly, it relates to a process for the production of detergent fatty alcohols. Still more particularly, it relates to a process for the production and refining of fatty alcohol products obtained by the hydrogenation of esters.

Fatty alcohols, or higher alcohols as they are sometimes designated, are monohydric aliphatic alcohols containing six or more carbon atoms which are derived either from natural sources or are synthesised from petroleum feedstocks. They are often classified by their market usage. As the primary end use of primary alcohols containing between about 6 and about 11 carbon atoms is the production of plasticiser esters, such alcohols are often termed plasticiser alcohols. For higher alcohols containing, for example, from about 11 up to about 20 carbon atoms, the major use is the production of synthetic detergents, hence such alcohols are often termed detergent alcohols. The distinction between plasticiser alcohols and detergent alcohols is somewhat arbitrary and detergent alcohols may have from 10 carbon atoms. In addition, there is some production of phthalate esters from a $C_{13}$ "oxo" alcohol and also some production of, for example, non-ionic surfactants from $C_8$ to $C_{10}$ alcohols.

Although there are some natural products which contain esters which can be hydrogenated to produce alcohols in the plasticiser range, these are more usually produced synthetically from petroleum feedstocks by, for example, the so-called "oxo" process, a process which is also termed oxonation or hydroformylation.

Detergent range alcohols, on the other hand, are typically produced by hydrogenation of low molecular alkyl esters of fatty acids. Such esters can be produced by transesterification of natural triglycerides or by esterification of the fatty acids obtained by hydrolysis of the triglycerides. Examples of triglycerides which can be used as raw materials include natural oils, such as coconut oil, rape seed oil, and palm oils, and animal fats such as lard, tallow, and fish oils. As such natural raw materials contain mixtures of triglycerides, the alcohol products obtained upon hydrogenation are also mixtures of n-alkanols of differing molecular weight.

One process for carrying out the esterification is described in U.S. Pat. No. 5,536,856 the contents of which are incorporated herein by reference. In this process, the esterification of the fatty acid is carried out in a column reactor having a plurality of esterification trays, each having a predetermined liquid hold-up and containing a charge of a solid esterification catalyst. The fatty acid flows down the column reactor against an upflowing lower alkyl alcohol vapour stream such as methanol. The supplied alcohol is relatively dry and water of esterification is removed from the top of the column in the vapour stream. The product ester is recovered from the sump of the reactor. As the liquid flows down the trays it encounters progressively drier lower alkyl alcohol which drives the ester reaction towards 100% conversion. The ester may then be fed to a polishing reactor operated under liquid phase conditions.

Once produced, these esters can be hydrogenated to the desired alcohols. However, as discussed in detail in U.S. Pat. No. 5,138,106, the contents of which are incorporated herein by reference, there is a problem in refining the product alcohol mixtures because one or more of the alkyl esters in the ester mixture which is subjected to hydrogenation will generally have boiling points close to that of one of the product alcohols making separation of any unconverted alkyl esters from the product alcohol mixture extremely difficult if not impossible.

The solution proposed in U.S. Pat. No. 5,138,106 is to use a process for recovering a fatty alcohol or alcohols from a fatty alcohol fraction containing a major molar amount of at least one fatty alcohol and a minor molar amount of at least one lower fatty acid ester comprising subjecting the fatty alcohol fraction to transesterification to convert substantially all of any lower alkyl fatty acid ester present in the feed mixture by ester interchange with a corresponding amount of fatty alcohol or alcohols to lower alkanol and to a wax ester derived from a fatty alcohol and a fatty acid. The lower alkanol is then separated from the reaction mixture by vaporisation to yield an intermediate transesterification product mixture that contains a fatty alcohol or alcohols and a wax ester or esters. This mixture is then distilled to yield an overhead fraction that contains the fatty alcohol or alcohols and is substantially free from lower alkyl fatty acid ester, and a distillation residue comprising fatty alcohol or alcohols and wax ester or esters. This residue is then subjected to a second transesterification in the presence of added lower alkanol to reconvert wax ester or esters to lower alkyl fatty acid ester or esters and to fatty alcohol or alcohols. Unreacted lower alkanol is then evaporated from the reaction mixture. The fatty alcohol or alcohols and the lower alkyl fatty acid ester or esters can then be recycled.

An alternative process for the production of fatty alcohols is described hi U.S. Pat. No. 5,157,168 the contents of which are incorporated herein by reference, in this process a fatty acid or mixture of fatty acids is esterified with a lower alkanol to form the corresponding fatty acid ester or esters. This ester or ester mix is then subjected to hydrogenation to give a product comprising a fatty acid or alcohols which are then refined. The conditions of both the esterification and the hydrogenation are selected such that the product stream is substantially free of ester.

A simplified version of one flow scheme for the production of fatty alcohols is illustrated schematically in FIG. 1. A fatty acid or mixture of fatty acids is subjected to esterification in the reactor 1. The product of the esterification reaction is withdrawn in line 2 and passed to vaporiser 3 where it is vaporised before being passed in line 4 to the hydrogenation reactor 5 where hydrogenation to desired alcohol occurs. The crude alcohol product generally has a residual alkyl ester content of about 2 to about 5 wt %. Although higher conversions may be achievable, this is coupled with a significant reduction in yield.

As discussed above, any residual lower alkyl ester can be particularly difficult to separate from the product alcohol and its presence can render the product of unacceptable purity for end users if the amount present is greater than about 0.15%. To address this, the product of the hydrogenation is then fed in line 6 to a wax ester reactor 7 where it is reacted in the presence of a liquid titania catalyst that is added in line 8. Here the residual ester, which is generally a methyl ester, is reacted with the product alcohol to form a wax ester via a homogeneously catalysed transesterification mechanism.

The product of the reaction is then passed in line 9 to the alcohol refining column 10 where the product alcohols can be separated readily from wax ester by conventional distillation. Product alcohols are removed in line 11. Lights are removed overhead in line 12 together with an alkane purge.

The residual wax ester could simply be removed. However, this would represent a loss to the economics of the process. The residual wax ester and the titania catalyst are therefore removed in line 13 and passed to a wax ester reversion reactor 14 where they are reacted with dry alcohol, such as methanol, added in line 15, in high molar excess. The wax ester is reverted back to the lower alkyl ester, such as the methyl ester, and product alcohol. The stream from the reversion reactor is then fed in line 16 to the vaporiser 3 where it is vaporised to separate the alcohol and the alkyl ester from the titania catalyst. A purge of heavies, including the titania catalyst, is removed from the vaporiser in line 17.

An alternative process is described in WO2013/072664, the contents of which are incorporated by reference, in which the use of a solid transesterification catalyst in the wax ester reactor enables the flow sheet to be altered to use a liquid phase hydrogenation on the bottom stream from the alcohol refining. By this means any unconverted ester present as wax ester in the refining zone bottom stream can be converted to product alcohol and then be returned to the distillation zone for recovery. In addition, the heavies can be removed from the liquid phase hydrogenation step.

The process described in WO2013/072664 for the production of fatty alcohol or alcohols comprises:
  (a) subjecting a fatty acid or fatty acid mixture to esterification with a lower alkanol in an esterification reactor maintained under esterification conditions to form a stream comprising the corresponding lower alkyl ester or esters;
  (b) vaporising the stream from step (a);
  (c) subjecting the vaporised stream of step (b) to hydrogenation in a first hydrogenation zone operated under hydrogenation conditions to form a stream comprising fatty alcohol or alcohols and an amount of unconverted lower alkyl ester or esters;
  (d) subjecting the stream from step (c) to transesterification in a wax ester reactor maintained under transesterification conditions in the presence of a solid transesterification catalyst thereby to convert at least a portion of the lower alkyl fatty acid ester by ester interchange with a corresponding amount of fatty alcohol or alcohols to lower alkanol and to a wax ester or esters derived from a fatty alcohol and a fatty acid;
  (e) separating fatty alcohol or fatty alcohols and wax ester or wax esters of step (d) by distillation to yield a fatty alcohol or alcohols product and a stream comprising wax ester or esters;
  (f) passing said stream comprising wax ester or esters to a second hydrogenation zone operating under conditions to effect hydrogenation in the liquid phase to revert the wax ester or esters to fatty alcohol or alcohols; and
  (g) returning the fatty alcohol or alcohols to the separation step (e).

In one described arrangement a heavies purge may be removed from the second hydrogenation zone. This purge may be passed to the vaporiser so that any product alcohol in the purge may be recovered.

The use of a solid transesterification catalyst in the wax ester reactor of step (d) and a liquid phase hydrogenation in step (f) allows at least a portion of any unreacted ester or esters from the hydrogenation step (c), and preferably all of any unreacted ester or esters from the hydrogenation step (c), to be converted into a wax ester or esters so that the ester or esters is not removed with the product alcohol or alcohols from the distillation step and then reverts the stream recovered from the distillation zone comprising the wax ester or esters to fatty alcohol or alcohols which can be recycled to the separating step (e). It should however be understood that the wax ester or esters stream recovered from the column bottoms of the refining step may comprise some fatty alcohol or alcohols.

This process offered various advantages. One benefit is that the make of alkane is minimised. In addition the wax ester or esters formed is free of metal and can readily be reverted by liquid phase hydrogenation. A particularly important benefit of this process is that the use of solid catalyst in the wax ester reactor means that $TiO_2$ deposits are not formed in the reactors. A still further advantage is that a lower amount of heavies needs to be purged thereby minimising the losses from the system.

Whilst the process described in WO2013/072664 offers various advantages, there is still a need to provide alternative processes which preferably address some or all of the problems of the prior art and which preferably improve the process efficiency of the reaction.

In particular, the growth in demand for naturally derived detergent range esters and alcohols such as those derived from coconut or palm kernel oils has driven a desire to provide improved processes.

In prior art systems such as that illustrated in simplified form in FIG. 1 the overhead stream 12 removed from the alcohol refining column 10 can have a high, typically around 50%, product alcohol content together with a mixture of alkanes and light components such as water and the lower alkanol that was used in the esterification reaction, for example methanol, comprising the balance. The residual alkanes in the stream are difficult, and in some cases impossible, to separate from the alcohols by refining and thus the stream cannot be recycled to the system. Thus the purge taken in line 12 represents a loss in the total process efficiency.

It has now been found that if the purge from the alcohol refining column is subjected to transesterification with a lower alkyl ester or esters taken from the initial esterification reaction to form wax esters the lower alcohol, water and other lights can be readily separated. The wax ester formed may then be treated to recover the desired alcohol.

Thus according to the present invention there is provided a process for the production of fatty alcohol or alcohols comprising:
  (a) subjecting a fatty add or fatty add mixture to esterification with a lower alkanol in an esterification reactor maintained under esterification conditions to form a stream comprising the corresponding lower alkyl fatty add ester or esters;
  (b) vaporising the stream from step (a);
  (c) subjecting the vaporised stream of step (b) to hydrogenation in a first hydrogenation zone operated under hydrogenation conditions to form a stream comprising fatty alcohol or alcohols and an amount of unconverted lower alkyl fatty add ester or esters;
  (d) subjecting the stream from step (c) to transesterification in a wax ester reactor maintained under transesterification conditions in the presence of a transesterification catalyst thereby to convert at least a portion of the lower alkyl fatty add ester or esters by ester interchange with a corresponding amount of fatty alcohol or alcohols to lower alkanol and to a wax ester or esters;
  (e) separating the stream from step (d) by distillation to yield a fatty alcohol or alcohols product steam; a wax ester or esters stream; and an overhead stream comprising fatty alkanol or alkanols and alkane, and optionally one or both of water and lower alkanol;
  (f) reading said overhead stream from step (a) in a wax ester reactor maintained under transesterification conditions in the presence of a transesterification catalyst with a lower alkyl fatty acid ester or esters thereby to convert at least a portion of the lower alkyl fatty acid ester by ester interchange with a corresponding amount of fatty alcohol or alcohols to lower alkanol and to a wax ester or esters; and (g) separating the wax ester or esters formed from the alkane, and any water and/or lower alkanol present.

The wax ester separated in step (g) may be treated by any suitable means to recover the desired product such that the overall efficiency of the reaction is improved. The recovery of the desired product may be a direct recovery or the wax ester may be recycled to the process and recovered indirectly or the wax ester may be treated and the product of the treatment may be recycled to the system.

In a preferred arrangement, the lower alkyl fatty acid ester or esters used in the transesterification reaction in step (f) is a portion of ester produced in step (a) of the process.

The term "fatty alcohol" means a linear alkanol containing from about 6 to about 26 carbon atoms. Preferred fatty alcohols contain from about 10 to about 20 carbon atoms. Thus in a preferred arrangement, the present invention relates to a process for the production of detergent fatty alcohols. Typical detergent fatty alcohols include hexanol, octanol, 1-decanol, 1-dodecanol, 1-tetradecanol, 1-hexadecanol, 1-octadecanol, 1-octadecenol and the like, and mixtures thereof.

The term "lower alkyl" means $C_1$- to $C_4$-alkyl, including methyl, ethyl, n-propyl, iso-propyl, n-butyl, iso-butyl and sec-butyl. The preferred lower alkyl radical is methyl. Similarly the term "lower alkanol" embraces $C_1$ to $C_4$ alkanols, including methanol, ethanol, n-propanol, iso-propanol, n-butanol, iso-butanol, and sec-butanol. Methanol is the preferred lower alkanol.

By the terms "fatty acid" and "fatty acids" we mean linear saturated, unsaturated or polyunsaturated aliphatic acids, such as linear alkyl, alkenyl, or hydroxyalkenyl carboxylic acids containing from about 6 to about 26 carbon atoms, preferably about 10 to about 20 carbon atoms. Examples of such fatty acids are decanoic acid (capric acid), dodecanoic acid (lauric acid), tetradecanoic acid (myristic acid), pentadecanoic acid, hexadecanoic acid (palmitic acid), heptadecanoic acid (margaric acid), octadecanoic acid (stearic acid or isostearic acid), octadecenoic acids (oleic acid, linoleic acid or linolenic acid), hydroxyoctadecenoic acid (ricinoleic acid), eicosanoic acid (arachidic acid) and docosanoic acid (behenic acid). Mixtures of fatty acids are of especial importance as raw materials from which the lower alkyl fatty acid esters used as starting material in the hydrogenation step are prepared. Such mixtures of acids can be obtained by hydrolysis of naturally occurring triglycerides such as coconut oil, rape seed oil, palm oils, tallow, lard and fish oils. If desired, such mixtures of acids can be subjected to distillation to remove lower boiling acids having a lower boiling point than a chosen temperature and thus produce a "topped" mixture of acids, or to remove higher boiling acids having a boiling point higher than a second chosen temperature and thus produce a "tailed" mixture of acids, or to remove both lower and higher boiling acids and thus produce a "topped and tailed" mixture of acids.

In a preferred process of the present invention esterification of the fatty acid or fatty acid mixture with the lower alkanol (e.g. methanol) is effected by a procedure in which the fatty acid or fatty acid mixture and lower alkanol are passed in countercurrent flow through a column reactor provided with a plurality of esterification trays mounted one above another, each adapted to hold a predetermined liquid volume and a charge of solid esterification catalyst thereon, liquid downcomer means associated with each esterification tray adapted to allow liquid phase to pass down the column reactor from that esterification tray but to retain solid esterification catalyst thereon, and vapour upcomer means associated with each esterification tray adapted to allow vapour to enter that esterification tray from below and to agitate the mixture of liquid and solid esterification catalyst on that tray, in which the fatty acid or fatty acid mixture is supplied in liquid phase to the uppermost one of said plurality of esterification trays whilst the lower alkanol is supplied in vapour form beneath the lowermost one of said plurality of esterification trays, in which vapour comprising lower alkanol and water of esterification is recovered from an upper part of the column reactor, and in which a lower alkyl fatty acid ester or ester mixture is recovered from a lower part of the column reactor.

In such a procedure the water content of the lower alkanol vapour supplied to the column reactor should be less than about 5 mole % and the number of esterification trays and the reaction conditions should be selected so that the stream of lower alkyl fatty acid ester or esters has a low acid content of less than about 1 mole %, calculated on a lower alkanol free basis, and an ester content, also expressed on an alkanol free basis, of at least about 99 mole %.

The process of the invention utilises the vaporous stream of the lower alkanol to carry away water of esterification produced in the esterification reactor but without carrying with it significant quantities of the fatty acid or acids or of the lower alkyl fatty acid ester or esters.

Any suitable reaction conditions can be used for the esterification in the esterification reactor. The esterification conditions used in the column reactor will normally include use of elevated temperatures up to about 160° C., for example a temperature in the range of from about 80° C. to about 140° C., preferably in the range of from about 100° C. to about 125° C. Such operating temperatures will be determined by factors such as the thermal stability of the esterification catalyst, the kinetics of the esterification reaction and the vapour temperature of the lower alkanol fed to the base of the column reactor at the relevant inlet pressure. Typical operating pressures at the vapour inlet of the column reactor range from about 0.1 bar to about 25 bar. A liquid hourly space velocity through the column reactor in the range of from about 0.1 $hr^{-1}$ to about 10 $hr^{-1}$, typically from about 0.2 $hr^{-1}$ to about 5 $hr^{-1}$, or about 2 $hr^{-1}$ may be used.

The fatty acid or fatty acid mixture is supplied in liquid form to an upper part of the column reactor or in admixture with lower alkanol, in solution in recycled ester product, or in solution in an inert solvent or diluent therefor. It is possible to pre-react the lower alkanol and the fatty acid or fatty acid mixture prior to introduction to the column reactor. The resulting reaction mixture contains a mixture of lower alkyl fatty acid ester or ester mixture, water, and lower alkanol.

Generally a vaporous mixture exits the column reactor as an overhead product. Provision may be made for scrubbing such vaporous mixture with lower alkanol in liquid form in order to wash traces of fatty acid ester and of fatty acid back into the column reactor. This overhead product from the column reactor can be condensed and treated in known manner to separate its constituents, the recovered water of esterification being rejected and the lower alkanol being recycled for re-use in as dry a form as is practicable within the relevant economic constraints. The lower the water content of the lower alkanol vapour that is supplied to the lowermost one of said esterification trays, the further towards 100% conversion to ester the esterification equilibrium reaction can be driven and the lower the residual acidity of the ester containing product recovered from the bottom of the column reactor will be. However, a balance may often have to be struck between the cost of providing, for example, a substantially dry lower alkanol for vaporisation into the column reactor, on the one hand, and the cost of providing and operating any additional downstream processing facilities that may be required to upgrade the ester product to the required quality if a less dry alkanol is used. This will vary from lower alkanol to lower alkanol and will depend upon the interaction between water and lower alkanol (e.g. azeotrope formation) and its effect upon alkanol/water separation. In any case, the water content of the lower alkanol vapour supplied to the reactor is less than about 5 mole %, and even more preferably is less than about 1 mole %.

The column reactor has a plurality of esterification trays. Although two or three trays may suffice in some cases, it will typically be necessary to provide at least about 5 up to about 20 or more esterification trays in the column reactor. Typically each esterification tray is designed to provide a residence time for liquid on each tray of from about 1 minute up to about 120 minutes, preferably from about 5 minutes to about 60 minutes.

A catalyst will generally be used for the esterification and this may be a solid catalyst although a liquid catalyst may also be used. Where the catalyst is a solid esterification catalyst, it may be a granular ion exchange resin containing $SO_3H$ and/or COOH groups. Macroreticular resins of this type are preferred. Examples of suitable resins are those sold under the trade marks "Amberlyst", "Dowex", "Dow" and "Purolite", such as Amberlyst 13, Amberlyst 66, Dow 0351 and Purolite 0150.

Different solid esterification catalysts may be used on different trays of the column reactor. Moreover different concentrations of solid esterification catalyst can be used on different trays.

The charge of solid particulate or granular esterification catalyst on each tray is typically sufficient to provide a catalyst to liquid ratio on that tray corresponding to a resin concentration of at least about 0.2% w/v for example, a resin concentration in the range of from about 2% w/v to about 20% w/v, preferably 5% w/v to 10% w/v, calculated as dry resin. Sufficient catalyst should be used to enable equilibrium or near equilibrium conditions to be established on the tray within the selected residence time at the relevant operating conditions. On the other hand not so much catalyst should be used on each tray that it becomes difficult to maintain the catalyst in suspension in the liquid on the tray by the agitation produced by the upflowing vapour entering the tray from below. For a typical resin catalyst a resin concentration in the range of from about 2% v/v to about 20% v/v, preferably 5% v/v to 10% v/v may be used.

The particle size of the catalyst should be large enough to facilitate retention of the catalyst on each tray by means of a screen or similar device. However, as larger catalyst particle sizes are more difficult to maintain in suspension and have lower geometrical surface area per gram, it is expedient to use not too large a catalyst particle size. A suitable catalyst particle size is in the range of from about 0.1 mm to about 5 mm.

Whilst a catalyst will generally be used for the esterification reaction, in one arrangement it may be autocatalysed.

One or more wash trays may be provided above the esterification trays in order to prevent loss of product, solvent and/or reagents from the column reactor.

In the hydrogenation zone of the process of the invention the lower alkyl fatty acid ester or esters are hydrogenated under vapour phase hydrogenation conditions in which the composition of the gas stream is selected so that at all times the material in contact with the hydrogenation catalyst is above the dew point, preferably at least about 5° C. above the dew point. Typical vapour phase hydrogenation conditions include use of temperatures of up to about 260° C., such as temperatures in the range of from about 140° C. to about 240° C., and pressures in the range of from about 5 bar to about 100 bar. Typically the hydrogen:ester mole ratio in the vaporous feed to the hydrogenation zone is at least about 100:1 up to about 2000:1 or more.

Suitable hydrogenation catalysts include ester hydrogenation catalysts such as reduced copper oxide-zinc oxide catalysts such as those described in GB2116552 and WO82/03854, and copper chromite, and promoted copper chromite catalysts. The preferred catalysts are reduced copper oxide-zinc oxide catalysts of the type disclosed in GB2116552 and WO82/03854. Such catalysts include reduced mixtures of copper oxide and zinc oxide derived from mixtures comprising, before reduction, (a) from about 10 to about 70 percent by weight CuO and about 90 to about 30 percent by weight ZnO, (b) from about 65 to about 85 percent by weight CuO and about 15 to about 35 percent by weight ZnO, and (c) from about 40 to about 50 percent by weight each of CuO and ZnO and 0 to 20 percent by weight of alumina. The preferred copper chromite catalysts are those containing from about 25 to about 45 percent by weight of copper and from about 20 to about 35 percent by weight of chromium, calculated as metal.

The hydrogenation mixture obtained by hydrogenating a lower alkyl fatty acid ester or mixture of esters contains, in addition to a fatty alcohol or fatty alcohol mixture, also lower alkanol, such as methanol. The lower alkanol is separated by any suitable means, such as by distillation in one or more stages, from the fatty alcohol or alcohols to yield a fatty alcohol fraction suitable for use in the process of the invention. Such a fatty alcohol fraction typically contains, besides possibly a minor molar amount of methanol or other lower alkanol, usually less than about 5 mole %, a major molar amount of a fatty alcohol or alcohols, usually about 90 mole % or more, and a minor molar amount of unreacted lower alkyl fatty acid ester or esters, usually from about 0.5 mole % up to about 5 mole %.

In the hydrogenation step of the process of the invention vapour phase conditions are used. In order to maintain all components in the vapour phase two important factors are (a) the hydrogen:ester molar ratio of the vaporous mixture to the hydrogenation zone and (b) the temperature thereof. In general, the higher the molecular weight of the lower alkyl fatty acid ester is, the less volatile it is and the higher its boiling point. Hence, for example, when using methyl laurate as a feedstock to the hydrogenation zone, a lower hydrogen:ester molar ratio and a lower inlet temperature to the hydrogenation zone can be used than when a higher boiling ester, such as methyl stearate, is to be hydrogenated. In practice a plant operator may wish to have the freedom to operate the process using fatty acids derived from different sources at different times. For example, he may wish to operate at different times using fatty acids from any of the common sources, such as tallow, lard, fish oil, coconut oil, rape seed oil or palm oil. A plant capable of handling such a range of acid feedstocks must be capable of hydrogenating the highest boiling methyl or other lower alkyl ester of a fatty acid that is likely to be used. Hence it must have an ester vaporisation section that can operate over a range of $H_2$:ester molar ratios and that can deliver to the hydrogenation zone a vaporous inlet mixture at the appropriate temperature, i.e. a higher inlet temperature and a higher $H_2$:ester molar ratio for methyl stearate, for example, than for methyl laurate.

The hydrogenation zone may comprise a single reactor operated under adiabatic conditions and containing a single bed of an ester hydrogenation catalyst, such as copper chromite or a reduced CuO—ZnO catalyst. In this case, however, the bed of catalyst must be sized so as to enable hydrogenation to be completed so far as possible by a single passage of the vaporous mixture therethrough at the design feed rate when operating at the lowest design temperature. In addition provision has to be made in designing the plant for any catalyst deactivation that may occur with ageing of the catalyst. If this approach is adopted then, with a catalyst charge that is sized for operation at a temperature suitable for a relatively low boiling ester, such as methyl laurate, it will be understood that, at the higher operating temperatures and higher hydrogen:ester molar ratios needed to maintain a high boiling ester, such as methyl stearate, in the vapour phase, hydrogenation occurs faster so that it is mainly the front end of the catalyst bed that is playing a part in the hydrogenation reactor, whilst the back end of the catalyst bed plays essentially no part. A disadvantage of this design approach is that, when operating with a high boiling ester, such as methyl stearate, the hot reaction mixture remains in contact with the catalyst for a significant time at the back end of the catalyst bed, although the hydrogenation reaction has effectively gone to completion, with the result that the conversion to by-products is correspondingly higher.

To address this, the first hydrogenation zone may have a plurality of beds, or sections of catalyst bed, of hydrogenation catalyst arranged in series which can be brought into use as required. In one arrangement the first hydrogenation zone has a main inlet and a main outlet, a plurality of beds of hydrogenation catalyst in the path of gas flowing between the main inlet and the main outlet, and one or more secondary flow connections each located between a respective pair of catalyst beds. The vaporous mixture containing hydrogen and lower alkyl fatty acid ester can be fed to the hydrogenation reactor by means of the main inlet whilst the reaction product is withdrawn either via the main outlet, so that all of the catalyst beds are used, or via one of the secondary flow connections, so that one or some only of the catalyst beds is or are used, depending upon the volatility of the ester, and hence upon the hydrogen:ester molar ratio and the inlet temperature of the vaporous mixture. Alternatively the reaction mixture can be withdrawn from the main outlet whilst the vaporous mixture is fed to one of the secondary flow connections. Any catalyst beds which are not in active use are maintained under an appropriate pressure of hydrogen. In this way the plant operator can readily select the appropriate number of beds of catalyst to suit the nature of the fatty acid feedstock currently being used.

The product of the hydrogenation is then passed to a wax ester reactor where transesterification to the wax ester occurs. The reaction is carried out in the presence of a solid transesterification catalyst. Any suitable transesterification catalyst may be used.

In one arrangement the transesterification catalyst may be a liquid catalyst or a solid catalyst.

Examples of suitable catalysts include alkyl titanates, alkali metal alkoxides, and metallic tin and stannous hydroxide, sulphuric acid, sulphonic adds, bases, compounds of alkali and alkaline earth metals, water and metals such as zinc, cadmium, lead and their compounds. Acidic resins containing, for example, —SO3H and/or —COOH groups or basic resins containing, for example, basic substituted ammonium groups can be used as transesterification catalysts. Other examples of transesterification catalysts included the alkali metal alkoxides, such as sodium methoxide or sodium ethoxide or an alkali metal alkoxide derived from the fatty alcohol product itself, or from one or more of them if a mixture of fatty alcohols is to be produced.

Further suitable catalysts include titanium silicate, cationic resins, zinc lanthanides, tungsten oxide on silica, zirconium sulphide, titanium based catalysts supported on cerium oxide or magnesium oxide. Further examples of suitable catalysts include "Amberlyst 15", "Amberlyst 16" or in the acid (R—SO$_3$H) and salt (R—SO$_3$Na) form of a sulphonic group or a carboxylic acid group. Further examples of suitable catalysts can be found in U.S. Pat. No. 4,681,967, EP0523461, EP0646567, U.S. Pat. No. 5,561,205, U.S. Pat. No. 5,436,357, WO98/28256, EP096487, EP0781758, WO99/47483, U.S. Pat. No. 6,204,424, U.S. Pat. No. 6,316,654, U.S. Pat. No. 6,359,157, U.S. Pat. No. 6,933,398, WO06/029655, U.S. Pat. No. 6,376,701, U.S. Pat. No. 6,743,942, WO07/043062, WO03/020782, WO07/111604, U.S. Pat. No. 7,030,057, WO04/085583, U.S. Pat. No. 7,211,681, EP1640356. WO06/070661, WO05/100306, U.S. Pat. No. 6,979,748, U.S. Pat. No. 7,078,560, U.S. Pat. No. 7,122,688, US2008/0021232, WO06/129435, WO07/074592, WO06/133437, WO07/025360, EP1785478, WO06/050925, US59088463, U.S. Pat. No. 6,147,196, WO07/006569, and WO06/013080 which are incorporated herein by reference.

The transesterification conditions will, to a large extent, depend upon the catalyst chosen. In one arrangement it may be carried out at a temperature of from about 150° C. to about 250° C. A pressure in the range of from about 2 psia to about 100 psia may be used with a pressure in the region of about 5 psia to about 50 psia being particularly useful. In one arrangement the catalyst may be in a fixed bed with a residence time of about 1 to about 5 hours.

The crude product liquid containing fatty alcohols, wax esters, catalyst and impurities will generally be passed to a refining column. The refining column will be operated under any suitable conditions. In one arrangement, the column operates under a vacuum at about 0.03 bara and uses structured packing. In one arrangement the middle sections of the column may contain a divided wall to separate the feed and product draws.

The overhead stream from the separation in step (e) is passed to a wax ester reactor maintained under transesterification conditions where it is subjected to transesterification with a lower alkyl fatty acid ester or esters to convert at least a portion of the lower alkyl fatty acid ester by ester interchange with a corresponding amount of fatty alcohol or alcohols to lower alkanol and to a wax ester or esters. In one arrangement, the lower alkyl fatty acid ester or esters will be a stream taken from the esterification reaction in step (a).

The transesterification reaction will generally be carried out in the presence of a catalyst. Any suitable catalyst may be used. The reaction may be homogeneous or heterogeneous. Examples of suitable catalysts are detailed above. The catalyst used for the transesterification of the overhead stream may be the same or different to that discussed above in connection with the wax ester reactor located between the hydrogenation reactor and the separation.

The lower alkanol, water and/or alkanes from the overhead stream may then be separated from the wax ester or esters. This separation does not suffer from the same difficulties as noted with the prior art processes. Separation may be carried out by any suitable means. Suitable means include via one or more of a flash or distillation step, optionally under vacuum conditions, by crystallisation or by membrane separation unit.

In one arrangement, the overhead wax ester will be treated with a lower alkanol, such as methanol, such that it is reverted to a lower alkyl ester and fatty alkanol. The lower alkyl ester and fatty alkanol may then be recycled to the vaporiser and hence to the hydrogenation reaction. This arrangement is particularly suitable where the catalyst is a homogeneous catalyst such as a titanate catalyst. In this arrangement the lower alkanol added to the wax ester reversion will generally be a dry lower alkanol.

In one arrangement the residual wax ester from the alcohol refining column may be passed to a residual wax ester reversion reactor where they are reacted with dry alcohol, such as methanol. The dry alcohol will generally be used in high molar excess. The residual wax ester is reverted back to the ester and product alcohol. The dry alcohol will generally be methanol. Following reversion, the stream may be recycled to the vaporiser and hence to the hydrogenation reaction. This arrangement may be particularly suitable where a homogeneous catalyst is used.

Where the residual wax ester from the alcohol refining column is subjected to this reversion reaction, the overhead wax ester found in the process of the present invention may be subjected to reversion in the same reactor or in a separate reactor. Thus in one arrangement the stream from the overhead wax reactor may be combined with the residual wax ester stream from the alcohol refining column before being passed to a single reversion reactor. In one alternative arrangement, the streams may be separately fed to the single reversion reactor.

By "dry alkanol" we mean that the amount of water present is about 1 wt % or less, and preferably less than 0.3 wt %.

In an alternative arrangement for the overhead reversion reactor, which is particularly suitable where a heterogeneous catalyst is used, the residual wax ester and lower alkanol, preferably supplied in high molar excess, are passed over the catalyst and reverted back to product alcohols and methyl esters which are then re-vaporised in the hydrogenation vaporiser.

An alternative arrangement, which is also particularly suitable where a heterogeneous catalyst is used, the residual wax ester and excess lower alkyl ester are subjected to a liquid phase hydrogenation and is converted to product alcohols which are then fed into the alcohol refining column and/or the ester removal reactor.

The reaction may be carried out in a continuous reaction or batch wise. A semi-batch wise arrangement may also be used. In one arrangement, where a batch wise arrangement is used, the overhead is collected, and then fed to a batch transesterification reactor. The reactor may be a stirred tank reactor charged with a suitable catalyst, such as alkyl titanate or an acidic ion exchange resin such as Amberlyst 16. The reaction may be carried out at any suitable temperature. The temperature selected will depend on the catalyst selected. Generally the reaction temperature will be in the region of about 100° C. to about 300° C. In one arrangement, the temperature will be in the region of from about 160° to about 240° C. In any event, the temperature will be selected to be sufficiently high to vaporise the lower alkanol liberated in the reaction.

The product from the batch reactor can be treated by any suitable means. In one arrangement, the product from the batch wax ester reaction may be heated in situ and distilled to remove light components such as residual lower alkanol, alkanes and alkanols before the wax ester is reacted in situ with lower alkanol to revert back to the alkyl ester or esters which may be fed to the alkyl ester vaporiser.

In an alternative arrangement to the overhead wax ester product to the alcohol refining column and the wax ester may be recovered from the bottom of the column.

A small purge of overhead will generally still be required to prevent a build up of alkanes in the system.

In a still further arrangement, once the wax ester is formed, the lights may be removed and the wax ester fed to a hydrogenation unit which hydrogenation, preferably a liquid phase hydrogenation, is carried out to the convert the wax ester or esters to alcohol or alcohols.

The aforementioned treatments of the overhead stream from the alcohol refining column may be applied to conventional processes in which the distillation residue which comprises wax ester is removed from the alcohol refining column and subjected to wax ester reversion in a wax ester reversion reactor in the presence of dry lower alkanol with the product optionally being returned to the vaporiser before being passed to the hydrogenation reactor.

In alternatives, the distillation residue from the alcohol refining column may be treated as described in WO2013/072664 in which the distillation residue is subjected to liquid phase hydrogenation in a second hydrogenation zone. The wax esters are hydrogenated on a fixed bed of catalyst typically consisting of components such as copper or copper-chromium oxide with secondary components such as zinc, aluminium, iron, silicon, and alkaline earth elements. The hydrogenation will be carried out at any suitable conditions. In one arrangement, the temperature will be from about 150° C. to about 240° C. or from about 180° C. to about 220° C. and a hydrogen pressure of from about 30 to about 150 bar or from about 40 to about 100 bar.

Alkane removal will generally occur at the same or higher temperature to the wax ester formation. However, it will generally be carried out at a reduced, vacuum, pressure such as at about 10 to about 500 mbara as alkane vapour pressure is much lower than that of the wax esters. The optimum pressure will depend on the chain lengths of the product alcohols being processed; a lower pressure will generally be more appropriate for a higher chain length. In may also be beneficial to reduce the pressure as lighter material is removed from the system.

The present invention will now be described by way of example with reference to the accompanying figures in which.

It will be understood by those skilled in the art that the drawings are diagrammatic and that further items of equipment such as reflux drums, pumps, vacuum pumps, temperature sensors, pressure sensors, pressure relief valves, control valves, flow controllers, level controllers, holding tanks, storage tanks, and the like may be required in a commercial plant. The provision of such ancillary items of equipment forms no part of the present invention and is in accordance with conventional chemical engineering practice.

Figure 1:
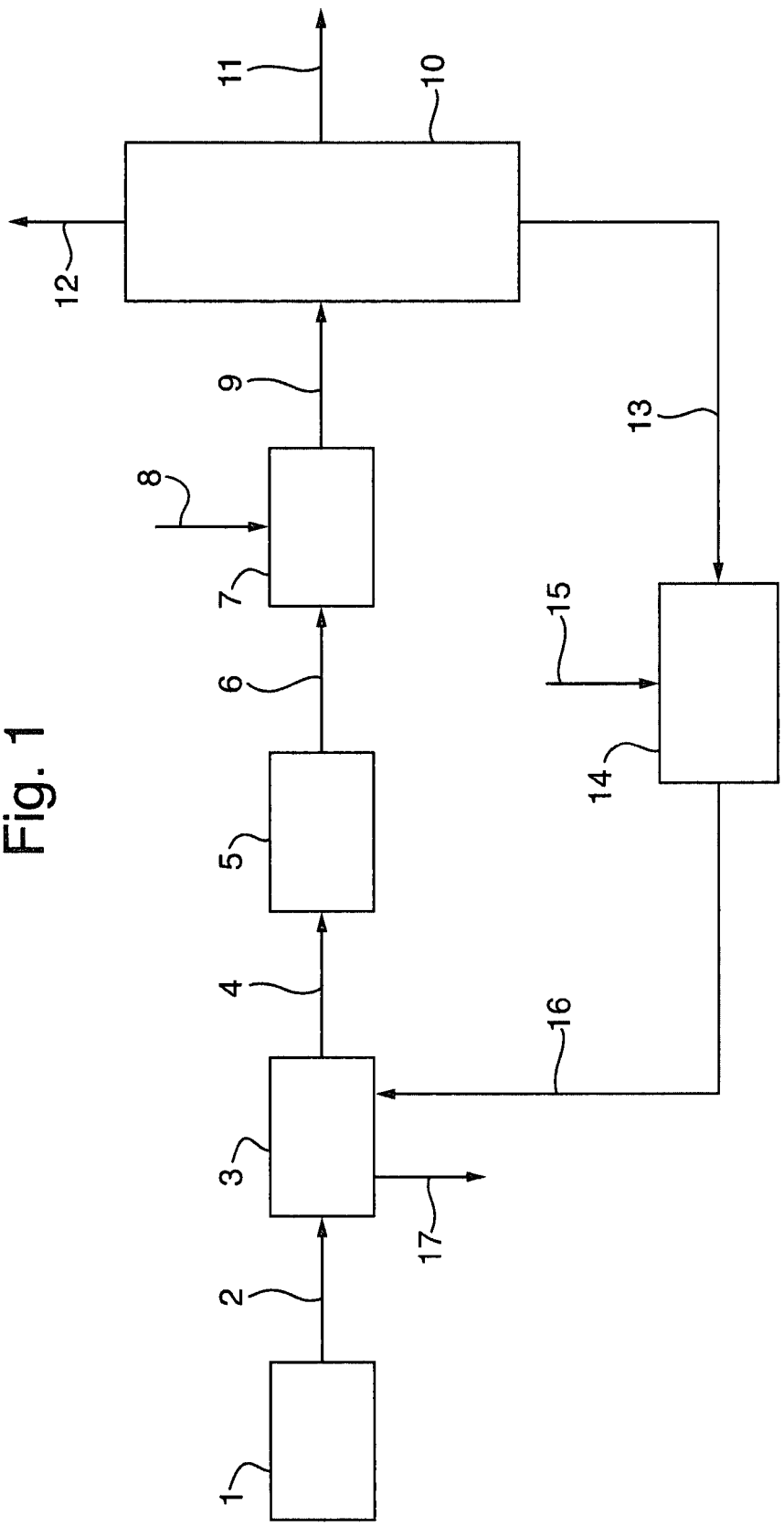
FIG. 1 is a schematic representation of a process according to the prior art.
Figure 2:
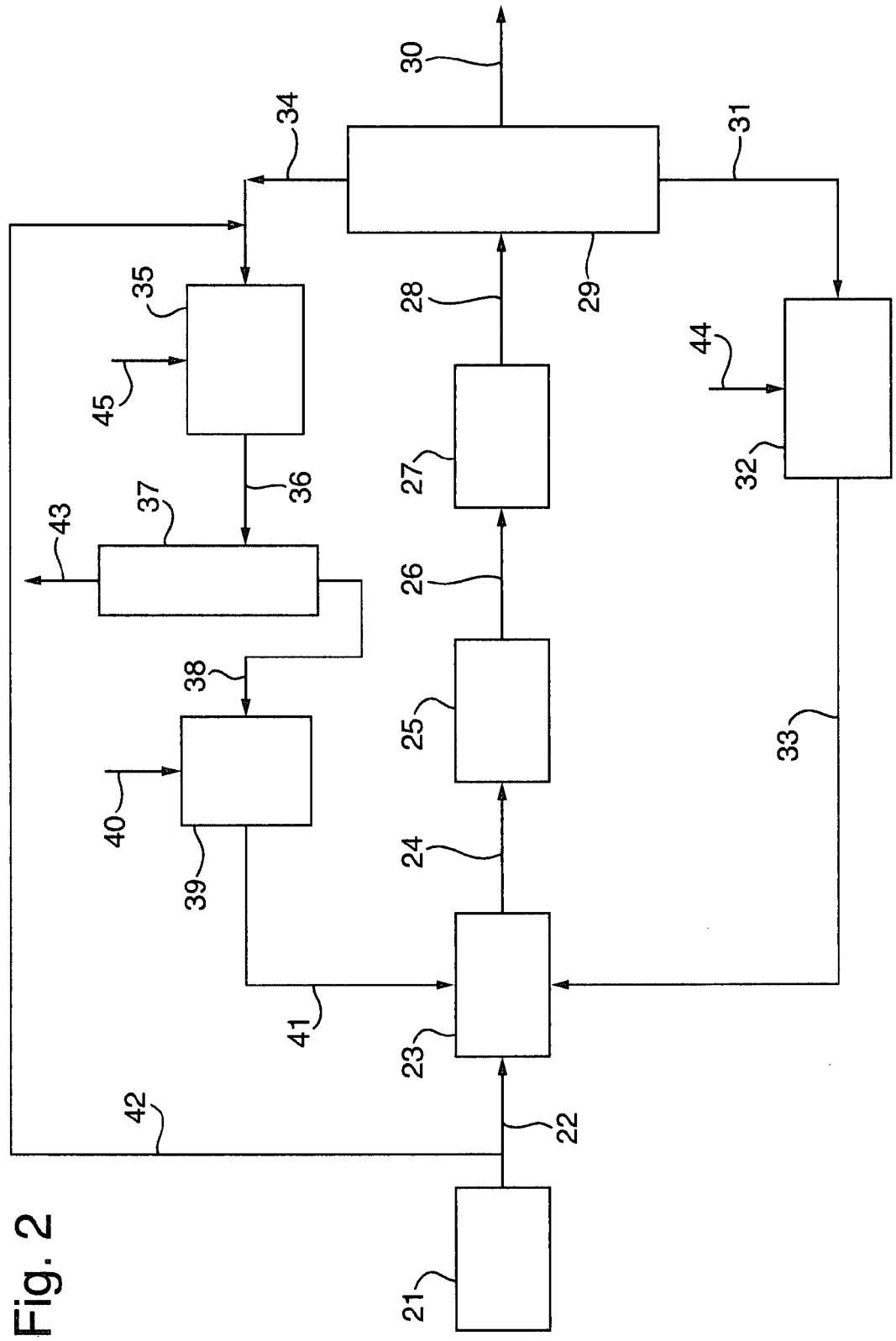
FIG. 2 is a schematic representation of the process of the present invention.

A simplified version of a one aspect of a flow scheme of the present invention is illustrated schematically in FIG. 2. A fatty acid or mixture of fatty acids is subjected to esterification in the reactor 21. The product of the esterification reaction is withdrawn in line 22 and passed to vaporiser 23 where it is vaporised. The vaporised stream is passed in line 24 to the hydrogenation reactor 25 where hydrogenation to the desired alcohol occurs. The crude alcohol product generally has a residual lower alkyl ester content of about 2 to about 5 wt %. Although higher conversions may be achievable, this is coupled with a significant reduction in yield.

As discussed above, any residual ester can be particularly difficult to separate from the product alcohol and its presence can render the product of unacceptable purity for end users if the amount present is greater than about 0.15%. To address this, the product of the hydrogenation is then fed in line 26 to a wax ester reactor 27 where it is reacted in the presence of a transesterification catalyst. Here the residual ester, which is generally a methyl ester, is reacted with the product alcohol to form a wax ester via a heterogeneously catalysed transesterification mechanism.

The product of the reaction is then passed in line 28 to the alcohol refining column 29 where the product alcohols can be separated readily from wax ester by conventional distillation. Product alcohols are removed in line 30. Lights are removed overhead in line 34. This stream includes alcohol, alkane, lower alkanol, and water.

The residual wax ester could simply be removed. However, this would represent a loss to the economics of the process. The residual wax ester are therefore removed in line 31 and passed to a bottoms wax ester reversion reactor 32 where it is reacted with dry alkanol such as methanol. The product of the reversion reactor is passed in line 33 to the vaporiser 23. In an alternative arrangement, the residual wax ester is passed directly to a liquid phase hydrogenation zone where the wax ester is at least partially converted to product alcohols and lower alkanol. This product is then fed directly to the wax ester reactor 27.

The overhead is passed in line 34 to an overheads wax ester reactor 35. Where a liquid catalyst is to be used this may be added in line 45. Following reversion the contents are passed in line 36 to the separator 37. The lights including lower alkanol, and alkanes are removed in line 43. A small portion of the product ester from reactor 21 may be fed in line 42 to the wax ester reactor 35.

The wax ester from the separator 37 is then passed in line 38 to a wax reversion reactor 39. It will be understood that the wax ester reversion reactors may be combined. However for clarity they are illustrated separately. Dry alkanol, such as methanol, is added to the reversion reactor 39 in line 40. The product is passed in line 41 to the vaporiser 23.

Figure 3:
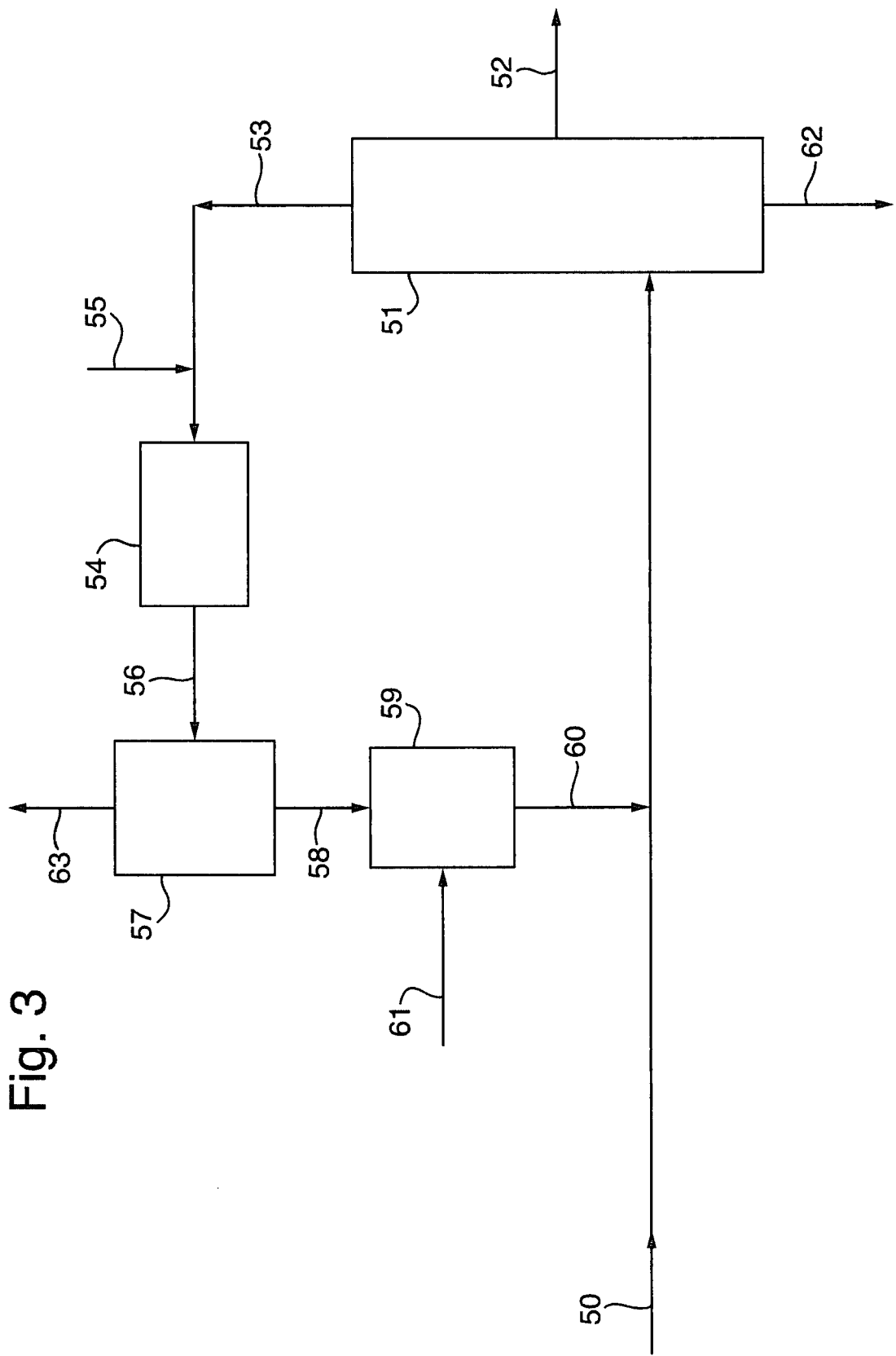
FIG. 3 is a schematic representation of an alternative process of the present invention.

An alternative arrangement is illustrated in FIG. 3. Here only the system after the hydrogenation is shown. In this process the wax ester is converted directly to alcohols via a liquid phase hydrogenation unit.

The product stream from the overheads of the alcohol refining column may be combined with the wax ester stream exiting the bottom of the refining column prior to the liquid phase hydrogenation.

In this embodiment, the crude alcohol product following the wax ester reactor 27 from FIG. 2 is passed in line 50 to the alcohol refining column 51. Product alcohols are removed in line 52. Residual wax ester is removed from the column 51 in line 62.

The overheads in line 53 are mixed with lower alkyl ester added in line 55 before being passed to the wax ester reactor 54. This will generally be a heterogeneous wax ester reactor. The product is removed in line 56 and passed to a separator 57. The lights are removed in line 63. The wax ester is passed in line 58 to a liquid phase hydrogenation reactor 59 where it is contacted with hydrogen which is added in added in line 61. The hydrogenation will generally take place over a suitable catalyst. The product from reactor 59 is then fed back to column 51 via line 60.

The present invention will now be described with reference to the following examples.

EXAMPLE 1

To simulate a transesterification of the commercial refining column overheads stream, reactants were charged to a round-bottomed flask fitted with a condenser, overhead stirrer and nitrogen purge. The flask was heated using a mantle and packed with insulation to maintain a constant temperature. When at temperature the catalyst was introduced to the flask and samples taken at time intervals of 5, 15, 30, 45, 60, 90, 120, 180 and 240 minutes. The samples were analysed by GC method.

Due to the potential inaccuracies in weighing out small masses of catalyst for these experiments, an excess of catalyst was diluted into an appropriate mass of dodecanol and this mixture added to the heated reaction flask to start the experiment (t=0). Full composition data for each run is set out in Table 1.

TABLE 1

Summary of CSTR reaction rate data for transesterification of a simulated lights purge stream from refining.

| Test | Catalyst Charged g | Ester:Alcohol mol | Temp °C. | Wt % $C_{12}$ alcohol conversion at time/min | | | | | | | | |
|---|---|---|---|---|---|---|---|---|---|---|---|---|
| | | | | 5 | 15 | 30 | 45 | 60 | 90 | 120 | 180 | 240 |
| 1 | 0.82 | 1.00 | 180 | 80.0 | 84.5 | 87.0 | 91.7 | 93.9 | 95.1 | 96.6 | 97.1 | 97.0 |
| 2 | 0.82 | 2.00 | 180 | 50.8 | 98.4 | 99.3 | 99.4 | 99.4 | 99.4 | 99.4 | 99.4 | 99.5 |
| 3 | 0.82 | 3.00 | 180 | 99.0 | 99.2 | 99.4 | 99.4 | 99.5 | 99.5 | 99.5 | 99.6 | 99.5 |
| 4 | 0.088 | 1.00 | 180 | 81.0 | 91.3 | 95.1 | 97.4 | 98.3 | 99.1 | 99.4 | 99.6 | 99.7 |
| 5 | 0.081 | 2.00 | 180 | 84.3 | 97.6 | 99.7 | 99.8 | 99.9 | 99.9 | 99.9 | 99.9 | 100 |
| 6 | 0.082 | 1.00 | 200 | 72.6 | | | | 95.0 | 96.5 | 97.4 | 98.3 | 98.7 |
| 7 | 0.086 | 1.00 | 220 | 72.6 | 83.9 | 90.3 | 93.5 | 94.9 | 96.6 | 97.4 | 98.2 | 98.6 |
| 8 | 0.087 | 1.05 | 220 | 78.5 | 89.3 | 93.2 | 94.9 | 95.9 | 96.7 | 97.4 | | |
| 9 | 0.018 | 1.00 | 180 | 15.3 | 41.3 | 62.1 | 78.3 | 85.2 | 92.1 | 94.6 | 97.2 | 98.2 |
| 10 | 0.026 | 1.00 | 220 | 15.2 | 43.7 | 71.4 | 84.8 | 91.4 | 96.2 | 98.0 | 99.2 | 99.6 |

Initial tests found very high reaction rates resulting in catalyst loadings being reduced to between 0.12 wt % (0.08 g) and 0.03 wt % (0.02 g) with respect to the methyl ester charge. Inconsistencies observed in the results were thought to be due to errors in measuring the small masses of catalyst charged to the CSTR during the test work and so latter testing used an appropriately diluted stock solution. Conversion is calculated in terms of C12 alcohol conversion rather than the more conventional C12 methyl ester conversion measure due to the use of excess methyl ester in some of these experiments. The CSTR composition during a typical run (Run 9) is set out in Table 2.

TABLE 2

Reactor Composition with Time for Run 1395/08

| Product Analysis wt % | Time (min) | | | | | | | | | |
|---|---|---|---|---|---|---|---|---|---|---|
| | 0 | 5 | 15 | 30 | 45 | 60 | 90 | 120 | 180 | 240 |
| C12 Aldehyde | 0.01 | 0.01 | 0.01 | 0.01 | 0.01 | 0.01 | 0.01 | 0.01 | 0.01 | 0.03 |
| C12 Alcohol | 31.42 | 26.60 | 18.45 | 11.92 | 6.83 | 4.65 | 2.48 | 1.69 | 0.86 | 0.55 |
| C12 Methyl Ester | 41.96 | 32.67 | 22.58 | 14.48 | 8.19 | 5.47 | 2.77 | 1.78 | 0.79 | 0.51 |
| C16 Alkane | 25.00 | 25.01 | 25.26 | 25.57 | 25.62 | 25.55 | 25.48 | 25.07 | 24.36 | 22.67 |
| C14 Alcohol | 0.08 | 0.07 | 0.05 | 0.03 | 0.02 | 0.01 | 0.01 | 0.01 | 0.01 | 0.00 |
| C24 Wax Ether | 0.00 | 0.036 | 0.069 | 0.094 | 0.114 | 0.124 | 0.132 | 0.135 | 0.139 | 0.146 |
| C24 Wax Ester | 0.86 | 14.95 | 32.85 | 47.12 | 58.41 | 63.33 | 68.25 | 70.45 | 72.93 | 75.13 |
| C26 Wax Ester | 0.11 | 0.08 | 0.18 | 0.27 | 0.34 | 0.39 | 0.42 | 0.45 | 0.47 | 0.49 |
| Others | 0.57 | 0.57 | 0.56 | 0.51 | 0.47 | 0.46 | 0.45 | 0.42 | 0.44 | 0.47 |
| Conversion (Wt %; C12 Alcohol basis) | 0.00 | 15.32 | 41.28 | 62.07 | 78.25 | 85.20 | 92.12 | 94.64 | 97.25 | 98.24 |

The invention claimed is:

1. A process for the production of fatty alcohol or alcohols comprising;
    (a) subjecting a fatty acid or fatty acid mixture to esterification with a lower alkanol in an esterification reactor maintained under esterification conditions to form a stream comprising the corresponding lower alkyl fatly acid ester or esters;
    (b) vaporising the stream from step (a);
    (c) subjecting the vaporised stream of step (b) to hydrogenation in a first hydrogenation zone operated under hydrogenation conditions to form a stream comprising fatty alcohol or alcohols and an amount of unconverted lower alkyl fatty acid ester or esters;
    (d) subjecting the stream from step (c) to transesterification in a wax ester reactor maintained under transesterification conditions in the presence of a transesterification catalyst thereby to convert at least a portion of the lower alkyl fatty acid ester or esters by ester interchange with a corresponding amount of fatty alcohol or alcohols to lower alkanol and to a wax ester or esters;
    (e) separating the stream from step (d) by distillation to yield a fatty alcohol or alcohols product steam; a wax ester or esters stream; and an overhead stream comprising fatty alkanol or alkanols and alkane, and optionally one or both of water and lower alkanol;
    (f) reacting said overhead stream from step (e) in a wax ester reactor maintained under transesterification conditions in the presence of a transesterification catalyst with a lower alkyl fatty acid ester or esters thereby to convert at least a portion of the tower alkyl fatty acid ester by ester interchange with a corresponding amount of fatty alcohol or alcohols to lower alkanol and to a wax ester or esters; and
    (g) separating the wax ester or esters formed from the alkane, and any water and/or lower alkanol present.

2. The process according to claim 1 wherein the wax ester separated in step (g) is treated to recover the desired product.

3. The process according to claim 1 wherein the lower alkyl fatty acid ester or esters used in the transesterification reaction in step (f) is a portion of ester produced in step (a) of the process.

4. The process according to claim 1 wherein the transesterification reaction of step (f) is carried out in the presence of a homogeneous or heterogeneous catalyst.

5. The process according to claim 1 wherein following transesterificatlon in step (f) the lower alkane and any alkanol and/or water from the overhead stream are separated from the wax ester or esters.

6. The process according to claim 5 wherein the separation is carried out via one or more of a flash or distillation step, by crystallisation or by membrane separation unit.

7. The process according to claim 1 wherein the overhead wax ester is treated with a lower alkanol such that it is reverted to a lower alkyl ester and fatty alcohol.

8. The process according to claim 7 wherein the lower alkyl ester is recycled to the vaporiser and hence to the hydrogenation reaction.

9. The process according to claim 1 wherein the residual wax ester from the alcohol refining column is passed to a residual wax ester reversion reactor and reacted with dry alcohol to revert the residual wax ester to the ester and product alcohol.

10. The process according to claim 9 wherein the ester and product alcohol are recycled to the vaporiser and hence to the hydrogenation reaction.

11. The process according to claim 7 wherein the residual wax ester and lower alkanol are passed over catalyst and reverted back to product alcohols and methyl esters which are then re-vaporised in the hydrogenation vaporiser.

12. The process according to claim 7 wherein the residual wax ester and excess lower alkyl ester are subjected to a liquid phase hydrogenation and converted to product alcohols which are then fed into at least one of the alcohol refining column and the ester removal reactor.

13. The process according to claim 1 wherein the reaction is carried out one of batch wise and semi batch wise.

* * * * *